United States Patent [19]

Schlosberg et al.

[11] 4,277,326

[45] Jul. 7, 1981

[54] OXYGEN ALKYLATION OF PHENOL-CONTAINING HYDROCARBONACEOUS STREAMS

[75] Inventors: Richard H. Schlosberg, New Providence; Charles G. Scouten, Westfield, both of N.J.

[73] Assignee: Exxon Research & Engineering Co., Florham Park, N.J.

[21] Appl. No.: 95,641

[22] Filed: Nov. 19, 1979

[51] Int. Cl.$^3$ .................. C10G 19/08; C07C 41/00
[52] U.S. Cl. .................. 208/263; 208/8 R; 208/48 R; 568/630
[58] Field of Search ............. 208/263, 8 R; 568/749, 568/761, 630

[56] References Cited

U.S. PATENT DOCUMENTS

| 1,801,901 | 4/1931 | Britton et al. | 568/630 |
| 1,819,687 | 8/1931 | Miller | 568/761 |
| 3,617,513 | 11/1971 | Wilson et al. | 208/127 |
| 3,671,422 | 6/1972 | Morrow | 208/79 |
| 4,181,597 | 1/1980 | Yan et al. | 208/46 |

FOREIGN PATENT DOCUMENTS

| 866064 | 8/1978 | Belgium | 208/263 |
| 838900 | 3/1939 | France | 208/263 |
| 494450 | 10/1938 | United Kingdom | 208/263 |

OTHER PUBLICATIONS

Gardner et al. "Magnesium Hydroxide in Petroleum Industry" Ind. Eng. Chem. 24, 1141–1146, (1932).
Blom et al. Fuel 36, 135–153, (1957).
Yohe et al. J. Am. Chem. Soc. 69, 2644–2648, (1947).

Primary Examiner—Delbert E. Gantz
Assistant Examiner—G. E. Schmitkons
Attorney, Agent, or Firm—Henry E. Naylor

[57] ABSTRACT

Process for improving properties of phenol-containing hydrocarbonaceous streams such as a coal liquid by contacting stream with (a) a multivalent metal composition selected from the group consisting of oxides and/or hydroxides of multivalent metals capable of forming hydroxy metal phenates with the phenols of the stream; and (b) one or more alkylating agents represented by the formula RX where R is a $C_1$ to $C_{18}$ group selected from the group consisting of alkyl, allyl, cycloalkyl, haloalkyl, benzyl, and arylalkyl, provided X is located on the alkyl portions of the alkylating agent and X is sulfate or a halide.

28 Claims, No Drawings

OXYGEN ALKYLATION OF PHENOL-CONTAINING HYDROCARBONACEOUS STREAMS

BACKGROUND OF THE INVENTION

1. Field of the Invention

The present invention relates to improving the properties of phenol-containing streams, such as coal liquids and petroleum asphaltenes, by oxygen-alkylation. The resulting upgraded stream has improved storage and processing properties.

2. Description of the Prior Art

The viscosity of phenol-containing hydrocarbonaceous streams such as coal liquids and petroleum asphaltenes generally increases with time, thereby presenting problems in the storage and use of such liquids. Many of these liquids are rich in heteroatoms, and especially organic oxygen such as phenolic oxygen and carboxylic oxygen. It is believed that increases in molecular weight and consequently in viscosities are brought about in two ways: (1) by hydrogen bond formation and (2) by free radical initiated growth reactions.

Furthermore, because streams such as coal liquids are generally rich in phenolic and other polar functionality, they are not fully misible with petroleum liquids of comparable boiling point range which are usually less polar. Segregation of such streams can occur if mixed because the petroleum liquids, which generally lack highly polar groups, cannot participate in the intermolecular association between adjacent coal liquid molecules.

Although various methods have been proposed to eliminate or at least alleviate the aforementioned problems, there is still a need to develop more efficient and economical ways of improving properties such as the stability of such liquids.

SUMMARY OF THE INVENTION

In accordance with the present invention, properties such as storage and processing properties of phenol-containing hydrocarbonaceous streams are improved by converting phenol groups of the stream to ether groups via oxygen-alkylation.

The oxygen-alkylation process of the present invention comprises contacting the phenol-containing hydrocarbonaceous stream with (a) a multivalent metal composition selected from the group consisting of oxides and/or hydroxides of one or more multivalent metals capable of forming hydroxy metal phenates with the phenols of the stream, wherein said contacting is performed at temperatures lower than the decomposition temperature of the hydroxy metal phenates; and (b) one or more alkylating agents represented by the formula RX where R is a $C_1$ to about $C_{18}$ group selected from the group consisting of alkyl, allyl, cycloalkyl, haloalkyl, benzyl and arylalkyl, provided X is located on the alkyl portion of the alkylating agent and X is a sulfate or a halide selected from the group consisting of chlorine, bromine and iodine.

In a preferred embodiment of the present invention the hydrocarbonaceous stream is a coal liquid and the multivalent metal is selected from the group consisting of Ca, Ba, Sr and Ni where Ni has a valence of $+3$.

DETAILED DESCRIPTION OF THE INVENTION

Phenol-containing hydrocarbonaceous streams which can be treated according to this invention include, but are not limited to, those streams resulting from the processing of coal, petroleum, and those existing as impurities in such parent streams as linear paraffins.

The term phenol-containing hydrocarbonaceous stream means a hydrocarbonaceous stream containing measurable amounts of phenol compounds in which one or more hydroxyl groups are attached to an aromatic ring wherein the aromatic ring may also contain a heteroatom (e.g. nitrogen in a pyridine ring). Non-limiting examples of such phenol compounds include phenol itself (also known as benzophenol), the cresols, xylenols, recorcinol, naphthols, 8-hydroxyquinoline and 4-hydroxyquinoline. The phenol-containing hydrocarbonaceous stream, exlusive of the phenol-containing compounds, also contains at least 25 wt.% of compounds containing carbon and hydrogen, though other atoms (e.g. nitrogen, oxygen, sulfur) may also be present.

The present invention is not dependent on the method of producing the phenol-containing hydrocarbonaceous stream. For example, any coal liquid which contains phenols can be treated regardless of its method of production. Non-limiting examples of processes for producing coal liquids include pyrolysis, solvent refining, direct hydrogenation with or without a catalyst, catalytic or noncatalytic hydrogenation in the presence of a non-hydrogen donor solvent and catalytic or noncatalytic liquefaction by a hydrogen donor solvent method.

Although not wishing to be limited thereby, one preferred method for obtaining coal-liquids in the Exxon Donor Solvent (EDS) process for the liquefaction of coal and described in U.S. Pat. No. 3,617,513 incorporated herein by reference. Briefly stated, the EDS process involves the formation of a slurry of coal in a hydrogen-donor solvent, such as tetralin, maintained at elevated temperatures of about 260° to 370° C. under agitation. Holding the coal at these temperatures causes the coal to disintegrate and dissolve without the breaking of a significant number of coal covalent bonds thereby assuring only a limited amount of free radical formation. The slurry is held at these temperatures, under agitation, until the convertible portions of the coal are substantially uniformly dispersed in the hydrogen-donor solvent. When suitable dispersion is indicated, for example, by viscosity measurements conducted on the slurry, the temperature of the slurry is increased to bond-breaking or depolymerization temperatures above about 370° C. under a pressure effective to maintain the dispersed slurry substantially in liquid phase, generally about 350 p.s.i.g. In this second temperature stage, the dissolved coal particles are well dispersed in the hydrogen-donor solvent and the chance of hydrogen-donor stabilization of free radicals generated by bond breaking is maximized. At the same time, the chance for free radicals to combine with one another to produce undesirable molecules is minimized. The dispersed slurry is maintained at the elevated temperatures above about 370° C. until a predetermined conversion of the coal is obtained. The liquid, which contains phenols, is then distilled and hydrogenated, the gases drawn off, and the bottoms removed for coking and gasification.

In accordance with the present invention, the phenol-containing stream is treated with one or more multivalent metal oxides and/or hydroxides capable of forming hydroxy metal phenates with the phenols of the stream. The stream is contacted with the multivalent metal composition at a temperature below the decomposition temperature of the resulting hydroxy metal phenates; generally from about room temperature (20° C.) to the decomposition temperature of the hydroxy metal phenates. For example, when calcium is the multivalent metal of the multivalent metal composition used herein, the decomposition of its resulting hydroxy calcium phenate is about 490° C. The decomposition temperature of any resulting hydroxy metal phenate can be easily determined by one having ordinary skill in the art.

The amount of multivalent metal composition needed in the practice of this invention is dependent on the amount of multivalent metal required to react with a predetermined amount of phenols in the stream. Although it may be desirable to react as much of the phenols in the stream as possible, one may only wish to react, and convert to ethers, a certain maximum amount of phenols based on economic considerations.

The concentration of phenols in the hydrocarbonaceous stream can be determined by conventional analytical methods such as non-aqueous titration. The amount of multivalent metal need to react with a predetermined amount of phenols of the stream can be expressed as the mol ratio of metal (of the oxide and/or hydroxide) to phenolic-oxygen (in the stream). The preferred mol ratio of metal to phenolic-oxygen needed herein is that ratio which, when the metal oxide and/or hydroxides are contacted with the stream, will assure the reaction of at least about 15 wt. % of the phenols of the stream at a temperature of about 25° C. for a contact time of about 90 minutes. The wt. % of phenols reacted is based on the total weight of phenols in the stream.

It will be noted that because the activity of some metals is greater than that of other metals under a given set of conditions, less of the more active metal, for a given amount of phenols in the stream, is required to react with a predetermined amount of the phenols in the stream. For example, at a temperature of 25° C. and a contact time of 90 minutes, 17 wt. % of phenols are reacted in a phenol-containing coal liquid using zinc hydroxide at a metal to oxygen mol ratio of 1.0 whereas at the same temperature and metal to oxygen mol ratio, about 72 wt. % of phenols are reacted in the same coal liquid when calcium hydroxide is used. The relative activity of one metal to another is known in the art and the ratio of any given metal to oxygen can be determined by either routine experimentation or calculation by one having ordinary skill in the art.

The alkylating agent suitable for use herein can be comprised of one or more compounds represented by the formula: RX, where R is a $C_1$ to about $C_{18}$, preferably a $C_1$ to $C_4$ group selected from the group consisting of alkyl, allyl, cycloalkyl, haloalkyl, benzyl and arylalkyl provided X is located on the alkyl portion of the group and X is a leaving group such as sulfate or a halide selected from the group consisting of chlorine, bromine and iodine. Preferably X is chlorine and the haloalkyl is preferably a $C_1$ to $C_4$ chloroalkyl. The carbon atom to which X is attached must be a primary or secondary carbon, more preferably a primary carbon. Most preferred is when the alkylating agent is methyl chloride, methyl bromide, methyl iodide, dimethyl sulfate or mixtures thereof.

It will be noted that the alkylating agent can be prepared from its hydrocarbon precursor, for example, by free radical halogenation of alkenese or halogenation of hydrocarbon streams such as $C_1$ to $C_4$ gas streams obtained independently or as a result of petroleum or coal processing. The alkylating agent may also be prepared by the addition of sulfuric acid to olefins.

The phenols of the streams treated according to the present invention can be converted to ethers by contacting them with the reagents herein in several different ways. For example, both the multivalent metal composition and the alkylating agent can simultaneously be brought into contact with the stream. By this method the phenols are converted to ethers in situ and the resulting ethers become a component of the treated stream.

In another embodiment of the present invention the phenol-containing stream can be brought into contact with the multivalent metal composition, thereby forming hydroxy metal phenates which can then be separated and treated separately with the alkylating agent. The hydroxy metal phenates can also be dried before contacting with the alkylating agent.

In still another embodiment of the present invention, the phenol-containing stream can be contacted with the multivalent metal composition then separated into two streams. One stream would be substantially free of the resulting hydroxy metal phenates wherein the other would contain a high concentration of such phenates. Of course, such separation of the stream can be accomplished by any conventional technique, preferably by centrifuging.

It will be noted that it is desirable that the alkylation reaction takes place in the presence of a polar solvent in order to speed the rotation, dissolve the alkylating agent, or both. Non-limiting examples of such solvents are the dipolar, aprotic solvents selected from the group consisting of N,N-dimethyl-formamide (DMF), N,N-dimethylacetamide (DMAC), N,N,N,N-tetramethylurea (TMU), N-methylpyrrolidone (NMP) and the like as well as mixtures thereof.

In order to achieve a high percentage of phenol conversion to ethers with any given combination of multivalent metal compositions and alkylating agents, a multistage process can be employed. For example, the phenol-containing hydrocarbonaceous stream can be passed through a series of reaction vessels, each of which contains a predetermined amount of multivalent metal composition and alkylating agent. Of course the number of such vessels will vary depending on such factors as process conditions, concentration of phenols in the stream, mol ratio of multivalent metal to phenolic oxygen, activity of the multivalent metal composition, the activity of the alkylating agent, the economics of each additional conversion phenols to ethers, etc.

It may be desirable from an energy savings point of view that the phenol-containing hydrocarbonaceous stream be at elevated temperatures when contacted with the multivalent metal composition. In this context, elevated temperatures means temperatures greater than room temperature but lower than the decomposition temperature of the resulting hydroxy metal phenate. Generally, the phenol-containing feed stream will result from a chemical, petroleum or coal liquefaction process and will exit such process at elevated temperatures whereupon it can be treated directly with the multivalent metal composition, as long as the temperature of the stream is lower than the decomposition temperature of the resulting hydroxy metal phenate. Therefore, the temperature of the phenol-containing feed stream is dependent on the source and process for its production and may have to be cooled to a lower temperature before treating according to the present invention.

Preferably, it is desirable to treat the feed stream with the multivalent metal composition as close to the decomposition temperature of the resulting hydroxy metal phenate as possible. By doing so, the rate of reaction is increased and the addition of heat is not required to bring the feed stream up to an efficient reaction temperature. Therefore, if the feed stream exits a previous process already at elevated temperatures, and is treated according to the invention at those temperatures, an energy savings is realized because no external heat is needed for elevating the temperature of the feed stream to a more desirable reaction temperature.

Other methods which can be used in practicing the present invention are fluidized or fixed bed processes using phenol sorbent materials. Suitable phenol sorbent materials include basic ceramic sorbents such as barium titanate, calcium titanate, calcium aluminate cement, and the like.

Other conventional solid/fluid processes can also be used. Non-limiting examples of such other processes include cyclic fluid bed, tube flow reactor and moving bed processes.

Depending on the phenol concentration of the feed stream and the particular embodiment of the present invention which is employed, a high octane blending component for motor gasoline may be produced. That is, even if the phenols of the stream are converted in situ to ethers and remain part of the heated stream, the stream may still have value as an octane additive as long as the concentration of ethers is sufficient. Of course, the preferred streams suitable as high octane blending components are those streams which are formed primarily of only the ethers themselves.

Infrared analysis may be used to demonstrate that the phenol groups have been converted to ethers. If the added hydrocarbon group is IR-active, then the appearance of the appropriate infrared frequency is observed. Other well known analytical methods may also be employed if desired. The ultimate analysis of percent C, H, N, S and O is altered in a fashion which is consistent with the expected change owing to the added hydrocarbon substituent.

The following examples serve to more fully describe the manner of making and using the above-described invention, as well as to set forth the best modes contemplated for carrying out various aspects of the inventions. It is understood that these examples in no way serve to limit the true scope of this invention, but rather are presented for illustrative purposes. In all four examples of Table I the conversion of phenols to ethers was effectively 100%.

EXAMPLE 1

In a nitrogen-flushed glove bag, a 15-ml serum vial was charged with 1.7 gm of BaO (11 mmoles) and 10 ml DMF (N,N-dimethyl formamide). The vial was capped and 3 ml of raw coal naphtha containing approximately 10 wt. % phenols (phenol and cresols) was added via a syringe. 3 ml (28 mmoles) of alkylating agent, 1-bromobutane, was then added, also by syringe. The vial was vigorously shaken overnight (approximately 21 hours), then centrifuged to precipitate insoluble salts. The clear supernatent liquid was separated and analyzed by gas chromotography (GC) for unreacted phenols and corresponding butyl aryl ethers. Quantitative conversion of phenols to alkyl aryl ethers was indicated both by the amount of product formed as well as by the absence of free phenols in the treated stream. Similarly, analysis of extracts from acidified insoluble salts indicated the absence of unreacted phenol residues. All materials were handled under nitrogen to exclude oxygen and moisture from the air. Reactions were carried out in serum vials with teflon-faced silicone septa.

EXAMPLES 2-5

Additional experiments were performed according to the procedure set forth in Example 1 above. In each experiment 3 ml of naphtha and 10 ml of DMF were employed and the amounts of other ingredients is set forth in Table I below:

TABLE I

| Example | Naphtha | mmols BaO | Alkylating Agent (AA) | mmol of AA |
|---|---|---|---|---|
| 2 | syn.[1] | 8.22 | n-$C_4H_9I$ | 2.63 |
| 3 | syn.[1] | 8.15 | n-$C_4H_9Br$ | 3.15 |
| 4 | raw coal naphtha[2] | 9.26 | n-$C_4H_9I$ | 2.63 |
| 5 | raw coal naphtha[2] | 9.39 | n-$C_4H_9Br$ | 3.15 |

[1] Synthetic naphtha - a toluene solution containing phenol (0.5M), O-cresol (0.1M), m-cresol (0.2M), p-cresol (0.31M) and 0.5 mol. % n-$C_{16}H_{34}$ (internal standard for GC analysis).

[2] raw coal naphtha from Exxon Donor Solvent process containing approximately 10 wt. % phenols (phenol; 0, M, p-cresols, and trace of $C_2$ phenol). 0.5 mol. % of n-$C_{16}H_{34}$ was added, prior to treatment, to the raw coal naphtha as an internal standard for GC analysis.

EXAMPLE 6

A 300 cc stirred autoclave was charged with 100 gm of raw coal naphtha, containing about 10 wt. % phenols, 7.64 gm of Ca(OH)$_2$ (1 Ca for each oxygen in the naphtha) and 41.1 g of n-bromobutane (3 molar excess based on the oxygen contained in the naphtha). The mixture was slurried and heated at a temperature of about 200° C. for 3 hours. Total contact time of ingredients with coal naphtha was approximately 3 hrs and 45 minutes. After cooling, the resulting solids were separated and the clear supernatant liquid was analyzed by GC. Some unreacted phenols were found, together with the butyl ethers of phenol and the isomeric cresols in a combined amount corresponding to 49% conversion of the total phenols present.

What is claimed is:

1. A process for improving the properties of phenol-containing coal liquids by oxygen-alkylation which process comprises contacting the coal liquid with:
   (a) a multivalent metal composition selected from the group consisting of oxides and/or hydroxides of one or more multivalent metals capable of forming hydroxy metal phenates with phenols of the coal liquid, wherein said contacting is performed at temperatures lower than the decomposition temperature of the hydroxy metal phenates; and
   (b) one or more alkylating agents represented by the formula RX where R is a $C_1$ to about $C_{18}$ group selected from the group consisting of alkyl, allyl, cycloalkyl, haloalkyl, benzyl and arylalkyl, provided X is located on the alkyl portion of the alkylating agent and X is sulfate or a halide selected from the group consisting of chlorine, bromine and iodine.

2. The process of claim 1 wherein the multivalent metal is selected from the group consisting of Ca, Ba, Sr and Ni+++.

3. The process of claim 1 wherein the multivalent metal composition is a hydroxide.

4. The process of claim 3 wherein the multivalent metal composition is calcium hydroxide.

5. The process of claim 1 wherein the coal liquid contains a stoichiometric amount of water to hydrolyze any multivalent metal oxides to hydroxides.

6. The process of claim 1 wherein the alkylating agent is a $C_1$ to $C_4$ alkyl halide or alkyl sulfate.

7. The process of claim 6 wherein the alkylating agent is selected from the group consisting of methyl chloride, methyl bromide, methyl iodide, and dimethyl sulfate.

8. The process of claim 2 wherein the alkylating agent is a $C_1$ to $C_4$ alkyl halide or alkyl sulfate.

9. A process for improving the properties of phenol-containing hydrocarbonaceous streams by oxygen-alkylation, the process which comprises contacting the stream with:
(a) a multivalent metal composition selected from the group consisting of oxides and/or hydroxides of one or more multivalent metals capable of forming hydroxy metal phenates with the phenols of the stream, wherein said contacting is performed at temperatures lower than the decomposition temperature of the hydroxy metal phenates; and
(b) one or more alkylating agents represented by the formula RX where R is a $C_1$ to about $C_{18}$ group selected from the group consisting of alkyl, allyl, cycloalkyl, haloalkyl benzyl, and arylalkyl, provided X is located on the alkyl portion of the alkylating agent and X is sulfate or a halide selected from the group consisting of chlorine, bromine and iodine.

10. The process of claim 9 wherein the multivalent metal is selected from the group consisting of Ca, Ba, Sr and Ni+++.

11. The process of claim 9 wherein the multivalent metal composition is a hydroxide.

12. The process of claim 11 wherein the multivalent metal composition is calcium hydroxide.

13. The process of claim 9 wherein the stream contains a stoichiometric amount of water to hydrolyze any multivalent metal oxides to hydroxides.

14. The process of claim 9 wherein the alkylating agent is a $C_1$ to $C_4$ alkyl halide or alkyl sulfate.

15. The process of claim 14 wherein the alkylating agent is selected from the group consisting of methyl chloride, methyl bromide, methyl iodide and dimethyl sulfate.

16. The process of claim 10 wherein the alkylating agent is a $C_1$ to $C_4$ alkyl halide or alkyl sulfate.

17. A process for improving the properties of phenol-containing hydrocarbonaceous streams by oxygen-alkylation which process comprises:
(a) contacting the stream with a multivalent metal composition selected from the group consisting of one or more multivalent metals capable of forming hydroxy metal phenates with the phenols of the stream, wherein said contacting is performed at temperatures lower than the decomposition temperature of the hydroxy metal phenates;
(b) separating the hydroxy metal phenates from the treated stream;
(c) reacting the hydroxy metal phenate with one or more alkylating agents represented by the formula RX where R is a $C_1$ to about $C_{18}$ group selected from the group consisting of alkyl, allyl, cycloalkyl, haloalkyl, benzyl and arylalkyl, provided X is located on the alkyl portion of the alkylating agent and X is a sulfate or a halide selected from the group consisting of chlorine, bromine and iodine.

18. The process of claim 17 wherein the multivalent metal is selected from the group consisting of Ca, Br, Sr and Ni +++.

19. The process of claim 17 wherein the multivalent metal composition is a hydrxide.

20. The process of claim 19 wherein the multivalent metal composition is calcium hydroxide.

21. The process of claim 17 wherein the stream contains a stoichiometric amount of water to hydrolyze any multivalent metal oxides by hydroxides.

22. The process of claim 17 wherein the alkylating agent is a $C_1$ to $C_4$ alkyl halide or alkyl sulfate.

23. The process of claim 22 wherein the alkylating agent is selected from the group consisting of methyl chloride, methyl bromide, methyl iodide and dimethyl sulfate.

24. The process of claim 18 wherein the alkylating agent is a $C_1$ to $C_4$ alkyl halide or alkyl sulfate.

25. The process of claim 17 wherein the hydroxy metal phenate is dried before reacting with the alkylating agent.

26. The process of claim 17 wherein the hydroxy metal phenate is reacted with the alkylating agent in the presence of a polar solvent.

27. The process of claim 26 wherein the polar solvent is selected from the group consisting of N,N-dimethylformamide, N,N-dimethylacetamide, N,N,N,N-tetramethylurea, and N-methylpyrrolidone.

28. The process of claim 17 wherein the separation of the hydroxy metal phenates is done by concentrating the phenates in a minor portion of the feed stream.

* * * * *